United States Patent [19]

Hyodo et al.

[11] Patent Number: 4,697,925
[45] Date of Patent: Oct. 6, 1987

[54] METHOD OF MEASUREMENT USING SCATTERED LIGHT

[75] Inventors: Hiroshi Hyodo, Kyoto; Naoki Yamada; Kenichi Iwase, both of Joyo; Shinichi Kishimoto, Kuze, all of Japan

[73] Assignee: Kabushiki Kaisha Kyoto Daiichi Kagaku, Japan

[21] Appl. No.: 665,623

[22] Filed: Oct. 29, 1984

[30] Foreign Application Priority Data

Nov. 4, 1983 [JP] Japan .................................. 58-207728

[51] Int. Cl.⁴ ............................................ G01N 21/00
[52] U.S. Cl. ..................................... 356/339; 356/442
[58] Field of Search ............... 356/336, 337, 338, 339, 356/341, 441, 442

[56] References Cited

U.S. PATENT DOCUMENTS

| | | | |
|---|---|---|---|
| 3,200,700 | 8/1965 | Topol | 356/341 |
| 3,279,305 | 10/1966 | Muta et al. | 356/442 |
| 3,354,772 | 11/1967 | Topol | 356/338 |
| 4,058,736 | 11/1977 | Takahashi et al. | 356/427 |
| 4,283,143 | 8/1981 | Patterson | 356/339 |
| 4,329,591 | 5/1982 | Fujiwara et al. | 356/444 |
| 4,452,759 | 6/1984 | Takekawa | 356/442 |
| 4,558,947 | 12/1985 | Wardlaw | 356/336 |

FOREIGN PATENT DOCUMENTS

| | | | |
|---|---|---|---|
| 1458870 | 10/1966 | France | 356/442 |
| 189415 | 5/1964 | Sweden | 356/387 |

Primary Examiner—R. A. Rosenberger
Attorney, Agent, or Firm—Darby & Darby

[57] ABSTRACT

The test solution in the measuring cell is regarded to be divided into a plurality of sections, and the quantity of scattered light from each section is continuously measured to give a plurality of independent series of signal. This measurement is carried out by scanning the measuring cell with a minute light flux periodically to obtain a plurality of measurements in a period. Out of the series of signals obtained, those containing abnormal scattered light signal are eliminated to determine accurate concentration and reaction process.

12 Claims, 12 Drawing Figures

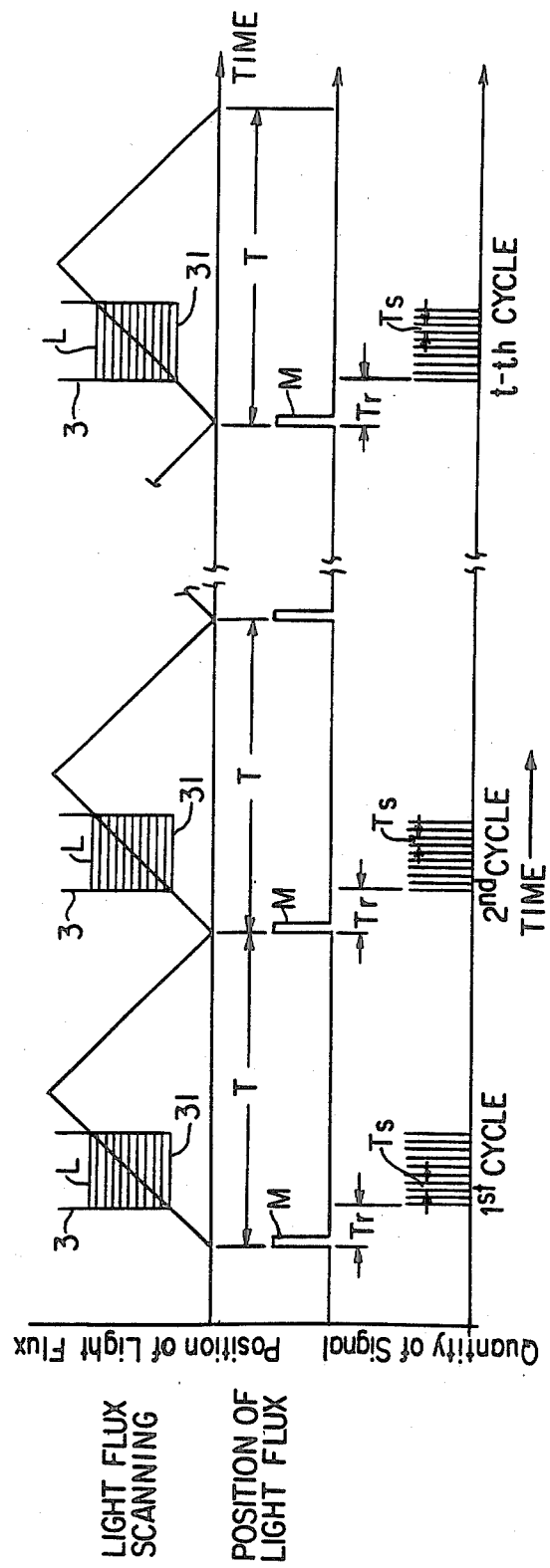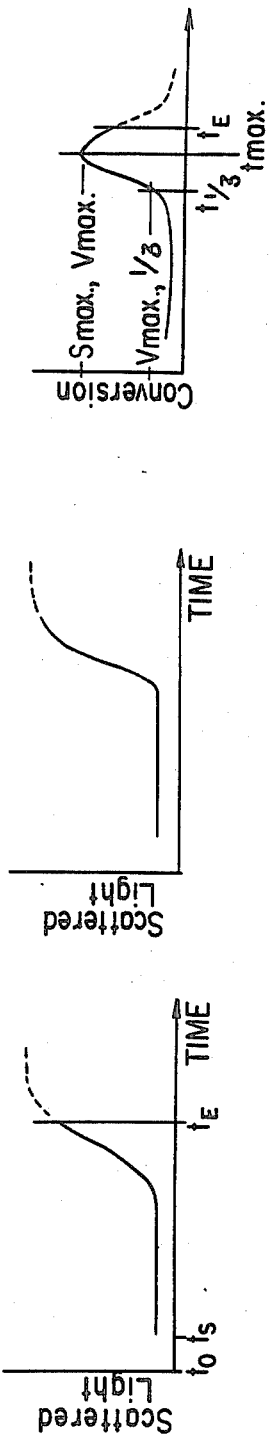

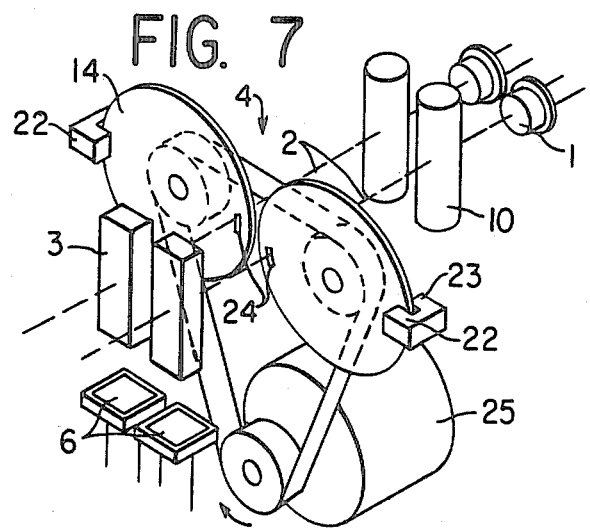
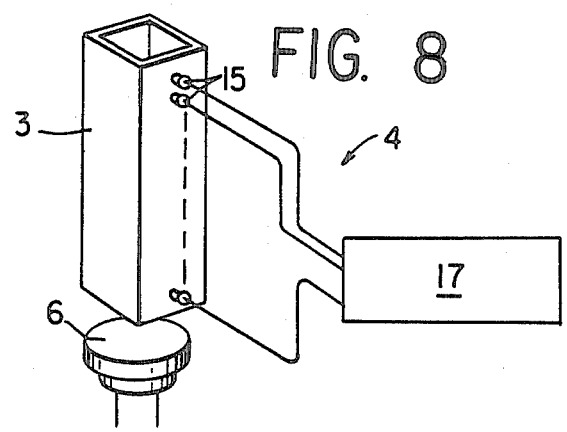
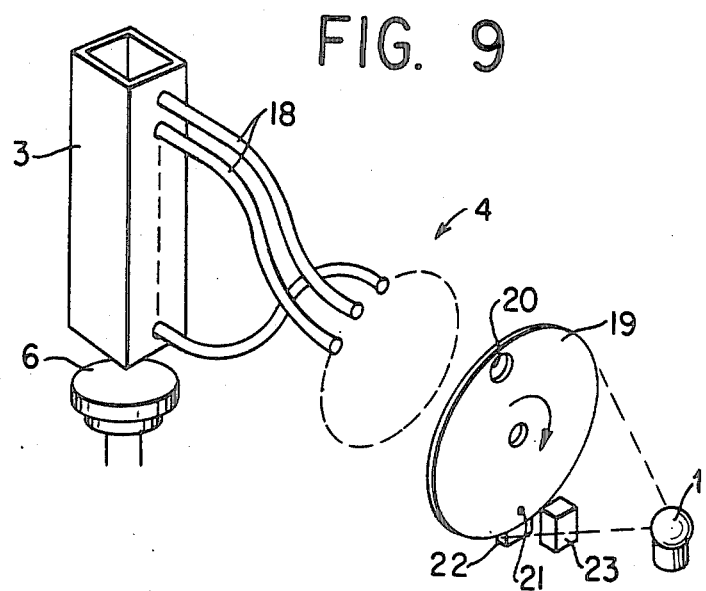

METHOD OF MEASUREMENT USING SCATTERED LIGHT

BACKGROUND OF THE INVENTION

This invention relates to a method of measuring the concentration of a substance or determining a reaction process caused in a sample solution, using scattered light. Particularly, the invention relates to a method which provides accurate understanding of partial reaction and effective removal of abnormal scattered light.

The measurement of scattered light is suited to the analysis of a reaction solution accompanied by the behavior of suspended material, because it is non-contacting with the reaction solution and more sensitive than tubidimetry. It is widely used in the field of clinical examination such as the measurement of various antigen-antibody reaction and blood coagulability test.

The conventional methods of scattered light measurement, however, have a drawback that they are susceptible to abnormal scattering due to dust or air bubbles mingled in the test solution, because they measure scattered light from a light beam incident upon the test cell in a relatively wide area. Particularly, when the concentration of the object to be measures is low and the level or change of the signal is small, the influence of abnormal scattering is remarkable, resulting in decreased reliability of measurement. To minimize the influence, a system is used in which light flux is applied to only a small part of the measuring cell. In this case, however, any dust or air bubble if present in the position where the light flux is applied can exert larger influence than that when light flux is applied to larger area.

To solve this problem another method (Japenese Laid-Open Patent Application No. Sho 57-23884) provides a noise detector independently from the detector for measuring the sample solution and remove the measurement signal obtained at the time when a noise is detected, from the calculation. In this technique, however, only one series of signals from a cell, or when dust, etc. are detected, a series of signals with a gap or gaps at the spot are obtained. When the gap or gaps are present in a significant position where the reaction process is determined, the measurement becomes meaningless.

Further, this Laid-Open Patent Specification No. Sho 57-23884 changes the relative position of the light flux application to the measuring cell whenever scattered light from dust, etc. is detected, or continuously moves the relative position during measurement to minimize the time the dust particle, etc. are in the flux. This method, however, is inaccurate since it treats the scattered light signals from different regions in the measuring cell without distinction to avoid the influence of dust, etc. When examining a reaction process, in particular, changing signals due to the difference of measuring region in the cell disturb the detection or reaction progress. This is fatal to the detection of reaction progress such as blood coagulability test and to reaction rate measurement.

In blood coagulability test, the coagulation time is defined as the time when fibrin separation begins to occur partially. When detecting the point where the reaction occurs partially, application of light flux over a wide range results in a small change rate of scattered light output and in poor reproducibility being susceptible to dust and air bubbles.

SUMMARY OF THE INVENTION

The present invention solves these problems in scattered light measurement at once.

The fundamental concept of the invention is to consider the test solution in the measuring cell divided into a plurality of regions. The quantity of scattered light in each region is continuously measured to give a plurality of independent scattered light output signal series. From the average of any one or a plurality of these signal series, the concentration of the test substance or the reaction process of the test solution is detected. By eliminating the signal series containing abnormal scattering signals in the time zone which affects the measurements, or all the signal series containing abnormal scattering signals, more accurate measurement is attained. Various methods and apparatus for materializing this principle are possible.

BRIEF DESCRIPTION OF THE DRAWINGS

FIG. 2 is an illustration showing the data sampling procedure on the apparatus as shown in FIG. 1;

FIG. 4 (a) is a type diagram of sampling data obtained in a region, FIG. 4 (b) is a type diagram of sampling data after noise has been removed, and FIG. 4 (c) is a graph showing the relationship between the signal change rate and time;

FIG. 7, FIG. 8, and FIG. 9 are perspective views each showing the essential parts of other apparatus different from each other.

DETAILED DESRIPTION OF THE INVENTION

Figure 1:
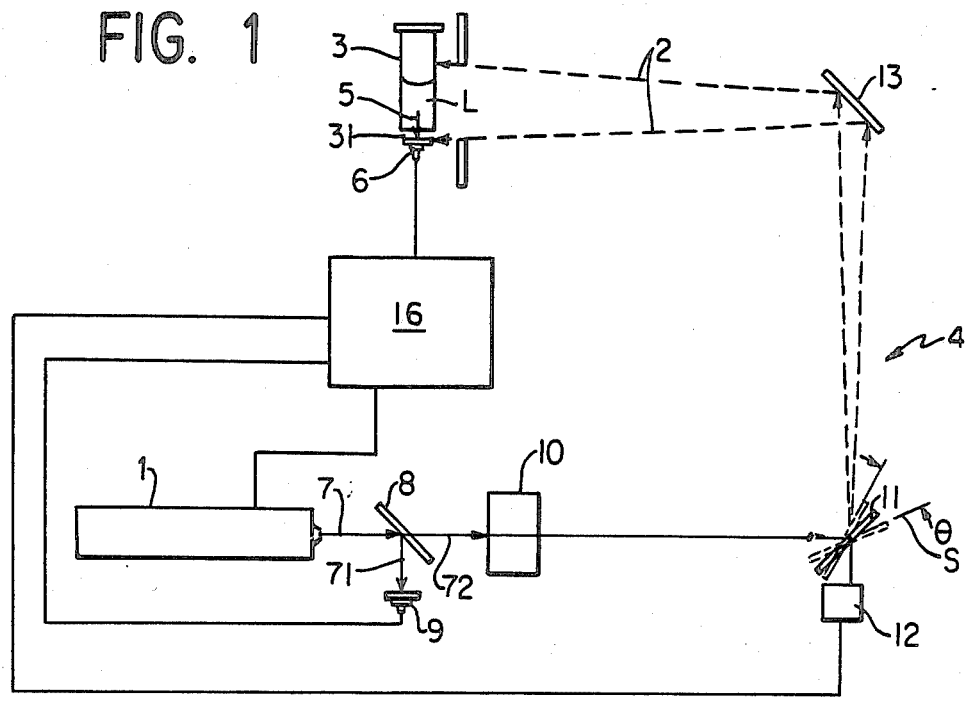
FIG. 1 is a block diagram showing an embodiment of the apparatus used in the invention.

Referring now to the drawings, the method of the invention will be detailed on an embodiment of the apparatus. Though the method according to the invention can be used for the analysis of any reaction which is accompanied by the behavior of a suspended material, the description here is made particularly on blood coagulation reaction as an example.

The apparatus shown in FIG. 1 is provided with a light source (1), an irradiation device (4) which applies the light from the light source (1) in the form of light flux (2) on the measuring cell (3) from the side periodically for canningg, a light detector (6) which is arranged under the measuring cell (3) and measures the intensity of scattered light (5) from the test solution (L), and a microcomputer (16) which receives and stores signals sent from the light detector (6 and sends out operating instructions to the whole apparatus.

The light source (1) is a He-Ne gas laser, and the laser ray 7) from the light source (1) is divided into two directions through a half mirror (8). One light flux (71) is applied to the reference light detector (9) as a reference light for light quantity correction. Another light flux 72) is laterally extended by a cylindrical lens (10) into a narrow belt like light flux (2) for measurement. The light flux (2) is applied on the measuring cell (3) by the action of a rotary mirror (11), rotary mirror driver (12), and reflecting mirror (13) as an irradiation device (4) and produced scattered light is measured by the light detector (6)

With reference to FIG. 2, the data sampling system according to the invention is now described.

The mirror (11) is driven at a constant speed, and goes and returns over an angle of $\theta$ from a mirror initialize position (S) in a period T. A mirror initialize signal (M) as the datum point for light flux scanning is first detected, and certain time Tr is measured from this point. The time Tr denotes the time required for the light flux (2) to move from the mirror initialize position (S) to the measuring cell bottom (31). A means to detect the measuring cell bottom (31) may be provided instead of detecting the mirror initializing signal (M) for starting reception of measurement signals, or the reception of measurement signals may be started after the bottom (31) of the measuring cell has been passed.

After time Tr has elapsed while the light flux (2) is scanning, a certain number n (10 in the drawing) of scattered light quantity data (measurement signals) are sampled every sampling period Ts. This divides the test solution (L) in the measuring cell (3) into n sections in longitudinal direction and provides scattered light information in each section in the first cycle at once. This number is determined by the moving distance, moving speed, and sampling period Ts of the light flux (2) in the position of the measuring cell (3).

Repetition of the action provides scattered light quantity information in n different sections of a reacting solution every T sec. in the 2nd cycle, 3rd cycle,...t-th cycle. These divided n sections may partially overlap or hold a gap between each other depending upon the width of the light flux.

This system is described on the case of blood coagulability test.

Figure 3A:
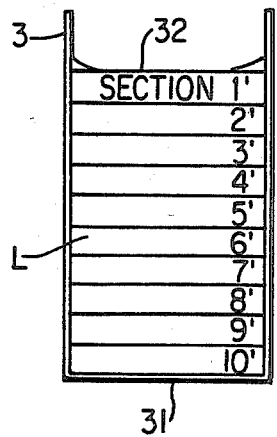
FIG. 3 (a) is a cross-sectional view of a measuring cell containing sample solution and FIG. 3 (b) is a graph representing a reaction pattern.
Figure 3B:
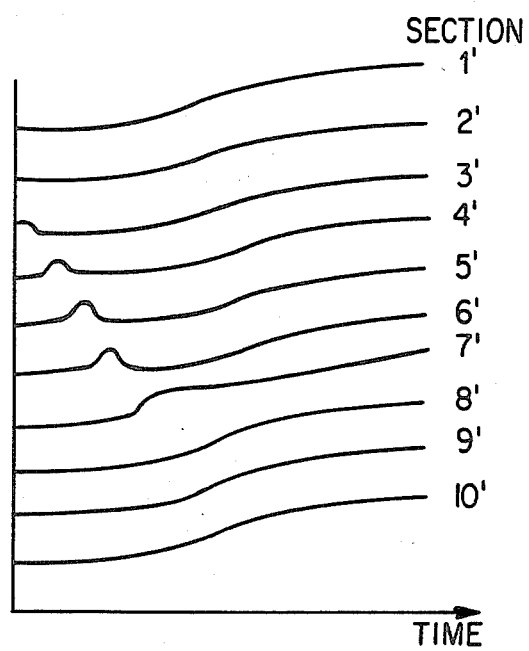

Assume that a reaction pattern four sections 1' through 10' shown in FIG. 3(b) is obtained when a test solution is measured divided into ten sections 1' through 10' as shown in FIG. 3(a). From FIG. 3(b), it is found that a noise component (dust, bubble, or crystal of reagent) settled down from section 3' to section 7' and stopped in section 7'.

If scattered light from a large area is to be measured as before, because the quantity of signals available is limited to one series, the measurement is influenced by noise components such as dust coming in or going out and moving in the optical field of vision. This will require complicated calculation to remove noise and the reliability of the results, if obtained, will have a problem. The system according to the invention, in contrast, will readily give results of high reliability by dealing with the sections which are free of noise.

As a method to obtain a result, blood coagulating time for example, from the series of signals from the sections 1-2 and 8-10 which are free of the influence of the noise component, it is possible to use the average of the results obtained by ordinary operation of the appearance time of the maximum reaction rate in each section or to use a value obtained from an adequate representative section. Further, if the noise component can be discriminated from the signal of reaction and is present in a time zone where it exerts no influence, such as before the reaction (signal series 3-6) or after the end of main reaction, the signal series from such sections can be dealt within the same manner as the signal series from the sections free of the influence of noise component.

FIG. 3(b) is a diagram of the output from the light detector (6) plotted for illustrating the principle of the invention. In the invention, the output signal is digitized and inputted into an arithmetic unit such as microcomputer (16) for certain operation and judgment. Sampled data are arranged for each section (an example is shown in FIG. 4(a)) and subjected to noise smoothing operation (FIG. 4(b)). In FIG. 4(a), to represent the measuring start point (reagent injection), ts, the light measuring start point (data sampling), and te, the light measuring end point. The noise smoothing is effected by obtaining the linear regression coefficient by the method of least squares for an item such as fibrin which shows smaller signal variation, and by obtaining moving average for other items such as PT (prothrombin time) and PTT (partial thromboplastin time). The coagulation time is determined in the former case (fibrin) as the time of maximum reaction (t max) (FIG. 4(c) 2) from the point where the linear regression coefficient (S) shows the maximum value (S max) (FIG. 4(c)), and in the latter case (PT and PPT) as the time (t $\frac{1}{3}$) (FIG. 4(c)) where the change rate is 1/n (n=3, for example) in FIG. 4(c) the maximum value (V max $\frac{1}{3}$) after being moving-averaged.

However, to obtain effective coagulation time of the whole sections, such discretion is used before determining these as the coagulation time as removing those of reaction rate higher than a level predetermined for each measuring item, or, to remove a peak caused by a foreign matter, those of reaction rate which drops to less than a certain proportion of the maximum value before a certain time is elapsed after the maximum value has appeared. Further, those which exceed the average by a certain proportion (±10% or ⊔20%, for example) are removed, and the average of the remainders or the least value of them is used for determining the coagulation time. And this value is converted into the concentration or activity according to the calibration curve for each measuring item.

As shown by the above description of one embodiment, the present invention permits catching the aspect of local reaction with time over the whole range of the test solution and provides detection of reaction products and background with high discriminating power.

Figure 5:
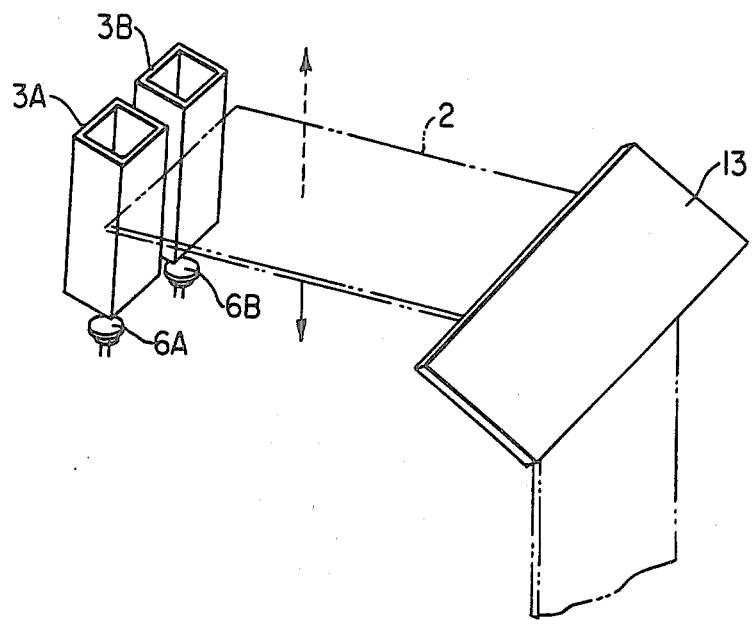
FIG. 5 is a schematic illustration when two measuring cells are simultaneously measured.

Though a preferred embodiment of the method and the apparatus of the invention has been described above, various modifications may be made without departing from the spirit of the invention, in which: First, the measurement may be made while scanning the cell (3) with the light flux (2) from the top surface of the cell (3) or liquid surface (32) to the bottom instead of from bottom to top of the cell (3). It is also possible to use two measuring cells (30 as shown in FIG. 5, measuring one cell (34) while the light flux 92) is ascending and the other cell (33) while the flux is descending. This will double the measuring efficiency. In this case, the output signals from the light detectors (6A and 6B) are alternately taken out and stored severally in the microcomputer (16). Further, it is possible to increase the number of cells to 4, 6, . . . , and in such cases to use unified cells to simplify the handling.

While in the above example the narrow belt-like light flux is moved up and down at the same speed, it can be moved slower on the onward way for measurement and faster on the return way for efficiency, or it can be swayed right and left. In addition to the above mentioned case, various light sources such as LED and tungsten lamp can be used as the light source (1). Further, the light flux (2) may be a spot light to irradiate narrower field of vision. And the spot light may be scanned in X and Y directions to cover the whole field of vision.

Figure 6:
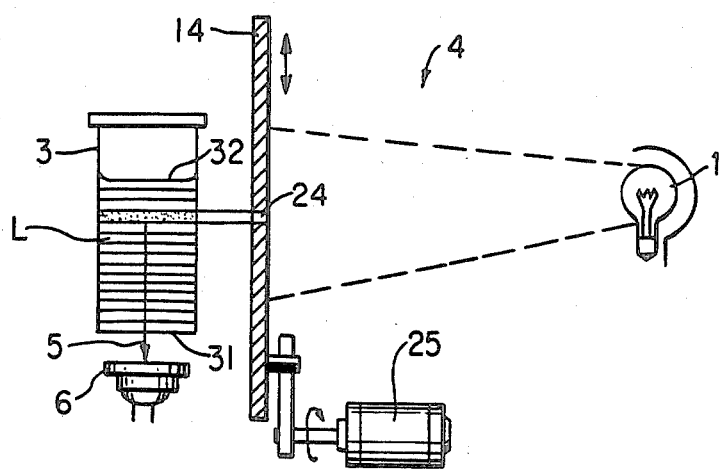
FIG. 6 is a side view showing the essential part of other apparatus.

As the rotary mirror driver (12), a pulse motor alternately driven in normal and reverse directions changed over periodically or a combination of synchronous motor and cam can be used. In this case, the movement of the light flux can be changed variously depending upon the shape of the cam. In addition to the use of a rotary mirror, the light source itself may be moved or a separating board (14) provided with a slit (24) shown in FIGS. 6 and 7 may be driven up and down (FIG. 6) or rotated (FIG. 7) by a motor. In FIG. 7, the symbol (22) represents the light source and (23) is a light detector to determine the datum position of the separating board (14).

FIGS. 8 and 9 show measuring apparatus of other types of system in which a measuring cell (3) is sectionally irradiated by a light flux (2) moving step by step and alight detector (6) successively measures the quantity of scattered light obtained intermittently from each section of the cell. In FIG. 8, individually independent light sources (15) such as light-emitting diode are used as the irradiation source and the irradiating device is provided with a changeover switch 17) which effects ON-OFF control in accordance with the instructions of the microcomputer (16). In FIG. 9, light from a light source (1) is irradiated on the side of the measuring cell (3) through optical fibers (18). The light is led through a hole (20) in a rotary plate (19) successively to each optical fiber bundle (18). A datum position of the rotary plate is determined based on a small hole (21) in the rotary plate (19), light source (22), and light detector 923), and the treatment is successively carried out with the scattered light at the time (scattered light output caused by the irradiation through the bottom optical fiber bundle, for example) as a standard output. In these apparatus, the light detector 96) obtains intermittent scattered light signals, but the treatment of the signals thereafter is same as in the case of continuous scattered light. In the apparatus in FIG. 6 and followings, it is recommended to use a half mirror (8) and correct the light quantity with a reference light detector (9) as in FIG. 1.

According to the present invention, as detailed above, in determining a reaction process in a test solution the concentration of a test substance in the measuring cell by the scattered light measuring system, spot-like or narrow band-like light flux is scanned in up-down and/or right-left direction to give a plurality of signals obtained from a plurality of sections of the measuring cell, the scanning is repeated to provide continuous measurements of the produced scattered light in each section, and the scattered light from each section in the measuring cell is measured continuously with time to determine the reaction process or the concentration.

Thus, the present invention provides accurate measurement without remeasuring even if any foreign matter such as dust and air bubble may be present locally in the measuring cell, by removing the measuring signals sent out from the local section the foreign matter is present.

On the other hand, in blood coagulation test, for example, where the blood coagulation time is defined by partial fibrin separation, it is not adequate to detect the condition after fibrin separation has spread in the whole cell. Even when a reaction itself proceeds locally in the measuring cell, the present invention provides accurate determination of reaction process such as coagulating time with high sensitivity by selectively using the signals from the relevant sections among a plurality of small sections.

What is claimed is:

1. A method of measurement using scattered light comprising the steps of:

scanning during each one of a plurality of successive scanning times each one of a plurality of sections of a test solution in a measuring cell with a minute light flux;

measuring the intensity of scattered light produced successively in each of said plurality of sections of the test solution during each successive scanning time;

producing from said successive measurements over time of the intensity of light from each of said plurality of sections of the test solution, an individual curve of light intensity versus time for each of said sections; and determining either the concentration or detecting the reaction process of the test solution from the average of a combination of said individual curves of light intensity versus time.

2. A method of measurement using scattered light as claimed in claim 1, wherein said light flux is irradiated on the measuring cell while continuously moving, and the intensity of scattered light is measured at regular time intervals as the intensity of scattered light from one such section.

3. A method of measurement using scattered light as claimed in claim 2, wherein the light from a light source is formed into a spot-like or narrow belt-like light flux and made to scan periodically a certain range of the measuring cell from the side, the output signals from a light detector positioned either above or under the measuring cell for measuring the intensity of scattered light are processed periodically from a datum point of time at certain time intervals in a specified number, and the received output signals are stored with time for every section.

4. A method of measurement using scattered light as claimed in claim 3, wherein said scanning of light flux is effected by either a spot-like or narrow band-like light flux reflected by a rotary mirror revolved in a certain range.

5. A method of measurement using scattered light as claimed in claim 3, wherein said scanning of light flux is effected by passing the light from the light source through either a small hole or a slit in a rotary plate or separating board rotated or move up and down.

6. A method of measurement using scattered light as claimed in claim 1, wherein said light flux is irradiated on each section of the measuring cell while moving stepwise and the intensity of scattered light in each section is measured in synchronism with the stepwise movement of the light flux.

7. A method of measurement using scattered light as claimed in claim 6, wherein a plurality of either spot-like or narrow belt-like irradiation sources arranged longitudinally on the side of the measuring cell is actuated orderly in one direction from a certain one, output signals from the light detector arranged above or under the cell for measuring scattered light intensity are successively processed, and the output signals are stored with time for every irradiation source.

8. A method of measurement using scattered light as claimed in claim 7, wherein said irradiation sources are independent from each other and the application of a power source to each irradiation source is selectively controlled.

9. A method of measurement using scattered light as claimed in claim 7, wherein said irradiation sources comprise the ends of optical fiber bundles which lead the light from the light source to respective positions, and the light is led to each end of optical fiber bundle through a slit in a rotary plate which is selectively rotated.

10. A method of measurement using scattered light as claimed in claim 1, wherein series of signals which contain abnormal light signals in a time zone which affects the measurement are removed from a plurality of series of signals, and the remaining normal signal series are used for either measuring the concentration or detecting the reaction process in the test solution.

11. A method of measurement using scattered light as claimed in claim 10, wherein either the concentration of the test substance or reaction process in the test solution is determined based on the average value of the series of normal signals.

12. A method of measurement using scattered light as claimed in claim 10, wherein either the concentration of the test substance or reaction process in the test solution is determined based on the average value of the series of normal signals excluding on series.

* * * * *